(12) United States Patent
Steinman et al.

(10) Patent No.: US 9,357,767 B2
(45) Date of Patent: Jun. 7, 2016

(54) ORGAN TRANSPORTER

(75) Inventors: Christopher P. Steinman, Sandy, UT (US); Rick W. Walker, Stow, OH (US); Kirk C. Palmerton, Kent, OH (US); Jeffrey S. Louis, Akron, OH (US); David Pettinato, Schaumburg, IL (US); Matthew Copithorne, Itasca, IL (US); Brian L Otts, Warrior, AL (US); Peter Demuylder, Ebbing (BE); James Guarrera, New York, NY (US); Ben O. Arrington, New York, NY (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 481 days.

(21) Appl. No.: 13/545,321

(22) Filed: Jul. 10, 2012

(65) Prior Publication Data

US 2014/0017770 A1    Jan. 16, 2014

(51) Int. Cl.
    *A01N 1/02*    (2006.01)
(52) U.S. Cl.
    CPC ............ *A01N 1/0247* (2013.01); *A01N 1/0273* (2013.01)
(58) Field of Classification Search
    None
    See application file for complete search history.

(56) References Cited

U.S. PATENT DOCUMENTS

| D531,320 | S  | 10/2006 | Garland et al. |
| 7,691,622 | B2 | 4/2010  | Garland et al. |
| 2005/0147958 | A1* | 7/2005  | Hassanein et al. ............. 435/1.1 |
| 2005/0221269 | A1* | 10/2005 | Taylor et al. .................... 435/1.1 |
| 2007/0275364 | A1* | 11/2007 | Hassanein et al. ............. 435/1.2 |
| 2008/0202969 | A1* | 8/2008  | Tauer .......................... 206/459.5 |
| 2011/0033916 | A1* | 2/2011  | Hutzenlaub et al. ........ 435/284.1 |
| 2012/0184024 | A1* | 7/2012  | Steen et al. ................. 435/284.1 |
| 2013/0164731 | A1* | 6/2013  | Cimino et al. ................. 435/1.1 |
| 2014/0169926 | A1* | 6/2014  | Henderson et al. ........... 414/800 |

FOREIGN PATENT DOCUMENTS

| WO | WO 02/26034 A2 | 4/2002 |
| WO | WO 2004-089235 A2 | 10/2004 |
| WO | WO 2009/041806 A1 | 4/2009 |
| WO | WO 2011037512 A1 * | 3/2011 |

OTHER PUBLICATIONS

Organ Recovery Systems LifePort Kidney Transporter; Work Instructions: Kidney Perfusion; published Sep. 30, 2008.*
Organ Recovery Systems LifePort Kidney Transporter;Operator's Manual; published 2003.*

(Continued)

*Primary Examiner* — Jill Warden
*Assistant Examiner* — Benjamin Whatley
(74) *Attorney, Agent, or Firm* — Oliff PLC

(57) ABSTRACT

A perfusion apparatus includes a coolant container having a basin-receiving recess that is at least partly surrounded by an inner chamber; a basin that is shaped to fit within the basin-receiving recess of the coolant container; and a cradle that is shaped to accept an organ and fit within the basin. The basin-receiving recess of the coolant container, the basin and the cradle each have positioning elements that are oriented such that the cradle is keyed to fit within the basin and the basin is keyed to fit within the coolant container, each in a single predetermined orientation. The plurality of positioning elements on the basin may include a plurality of protrusions on an outer surface of the basin.

22 Claims, 11 Drawing Sheets

(56) References Cited

OTHER PUBLICATIONS

LifePort Kidney Transporter Brochure, retrieved online Jul. 6, 2012 at "http://www.organ-recovery.com/pdfs/Kidney-Transporter-1-1/LifePort1.1_Brochure.pdf".

Order form from Organ Recovery Systems, retrieved online Jul. 9, 2012 at "http://www.organ-recovery.com/order_form.php.".

Jul. 8, 2013 European Search Report issued in European Patent Application No. PCT/US2013/049581.

Jul. 8, 2013 Written Opinion issued in European Patent Application No. PCT/US2013/049581.

"LifePort Kidney Transporter Work Instructions: Kidney Perfusion (Organ Recovery Systems)", Sep. 1, 2008, pp. 1-30.

"LifePort Kidney Transporter Operator's Manual", Jul. 21, 2007, pp. 1-47.

Jan. 13, 2015 International Preliminary Report on Patentability issued in International Patent Application No. PCT/US2013/049581.

* cited by examiner

US 9,357,767 B2

ORGAN TRANSPORTER

BACKGROUND

Related technical fields include organ or tissue perfusion apparatuses that are capable of sustaining and/or restoring viability of organs or tissue and preserving organs or tissues for diagnosis, treatment, storage and/or transport, and more particularly to an interrelationship between various components of the organ or tissue perfusion apparatus that come into contact with the organ or tissue and/or perfusate. For convenience, the term "organ" as used herein should be understood to mean organ and/or tissue unless otherwise specified.

It is an objective of organ perfusion apparatus to mimic the conditions of the human body such that the organ remains viable before being used for research, diagnosis, treatment or transplantation. Many times the organ needs to be stored and/or transported between facilities. A goal of sustaining and restoring organs during perfusion is to reduce ischemia and reperfusion injury. The increase in storage periods in a normal or near normal functioning state also provides certain advantages, for example, organs can be transported greater distances and there is increased time for testing, treatment and evaluation of the organs.

In maintaining organs in near ideal conditions and physiological states it is known to provide the organ in a cassette that allows for perfusing, storing, diagnosing, analyzing and/or transporting the organ. It is also known to provide the cassette in a compartment of an organ perfusion apparatus having a cooling structure.

U.S. Pat. No. 7,691,622 discloses, for example, a configuration in which an organ holding cassette may be disposed within a cooling compartment provided in a watertight container such that the walls of the cassette mate with a corresponding configuration of an inner transporter wall to maintain contact, and thus heat transfer, therebetween.

SUMMARY

When an organ or tissue is being harvested, it may be necessary to place the organ on a surface within the surgical environment to efficiently prepare the organ or tissue for transport, diagnosis, treatment and/or storage. Accordingly, it is desirable to provide a cradle that directly holds the organ or tissue and is easily inserted into, and is removable from, other apparatus and/or another removable part of the other apparatus. This allows for flexibility to the surgeon and/or medical assistants to move the cradle holding the organ, as needed, when the organ or tissue is harvested and/or is being prepared for transportation. It is also desirable to provide certain components of the apparatus as a packaged kit of sterile, disposable components to reduce cost and ensure that the parts of the apparatus that come into contact with the organ and/or perfusate are sterile.

DETAILED DESCRIPTION OF EMBODIMENTS

Figure 1:
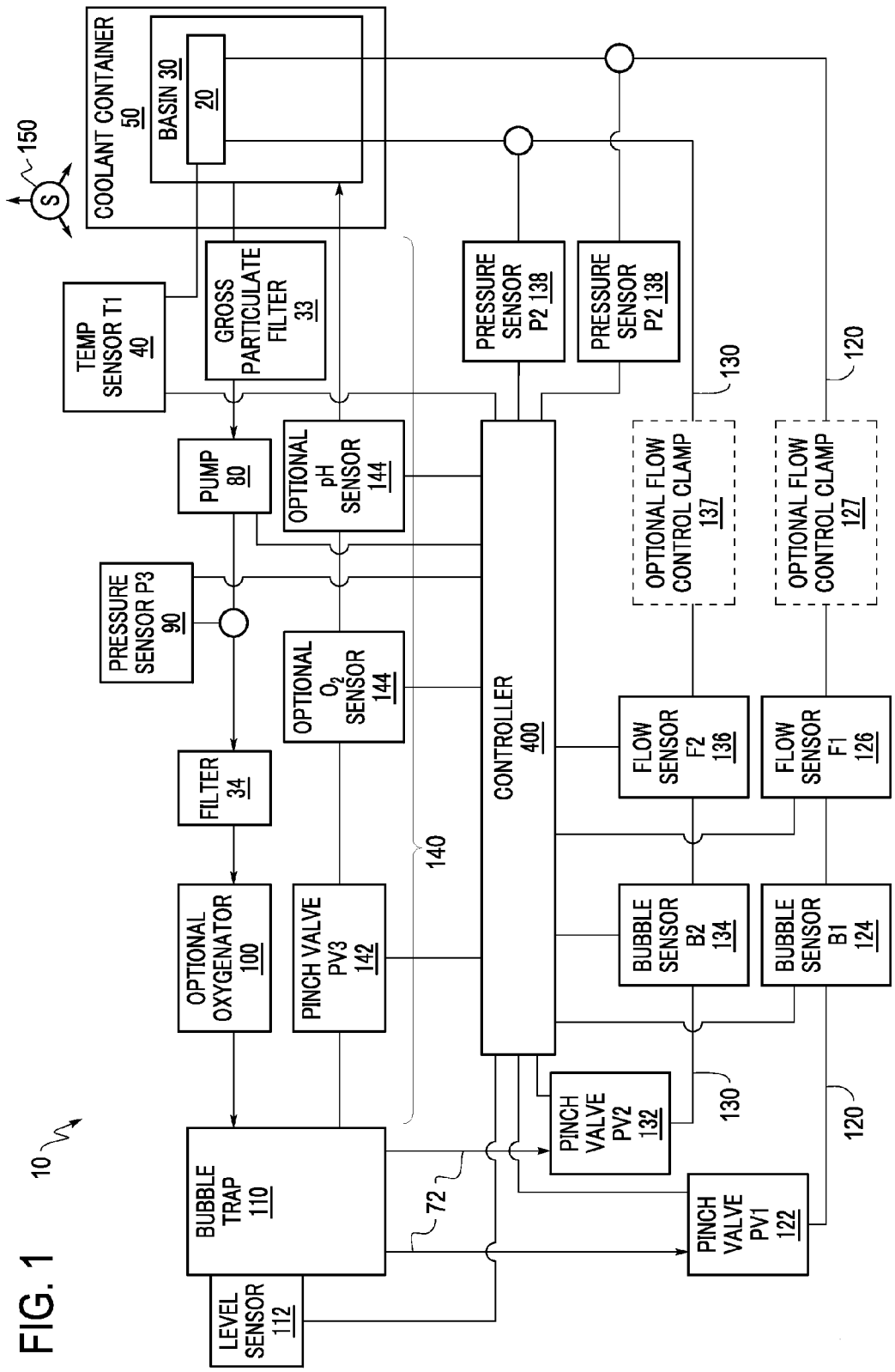
FIG. 1 is a schematic diagram of an organ perfusion apparatus.

According to exemplary implementations, an apparatus for holding an organ or tissue for at least one of perfusion, storage, treatment, diagnosis, and transport of the organ or tissue is provided. The apparatus may include a coolant container having an inner surface and an outer surface, the inner surface defining an inner chamber that is configured to contain a coolant, the outer surface forming a basin-receiving recess that is at least partly surrounded by the inner chamber. A basin may be provided that is shaped to fit in close proximity within the basin-receiving recess of the coolant container. The proximity of the outer surface of the basin to the coolant container may be controlled and a substantial surface area may be provided to maintain thermal conduction. In addition, one or more cradle may be provided that is shaped to fit within the basin and is configured to hold the organ or tissue. The surface of the cradle is preferably kept low inside the basin to ensure that a substantial amount of the cradle, and organ, is exposed to the perfusate solution thus maximizing thermal conduction between the organ and the perfusate solution. Preferably, the basin-receiving recess of the coolant container, the basin and the cradle each have a plurality of positioning elements such as protrusions and/or recesses that are oriented such that the cradle is keyed to fit within the basin and the basin is keyed to fit within the coolant container in a single predetermined orientation relative to one another. Preferably, the plurality of positioning elements on the basin includes a plurality of protrusions on an outer surface of the basin. At least one of the plurality of positioning elements on a bottom portion of the basin may extend below an otherwise lowermost portion of the basin. In some embodiments, the plurality of protrusions on the cradle may also act as feet when the cradle is not provided within the basin and is placed on a flat surface. The protrusions on the cradle may be sufficiently long to stably support the cradle when on a flat surface in spite of the exterior surface otherwise being substantially rounded.

In exemplary implementations, the plurality of positioning elements in the coolant container may include a plurality of recesses formed on a bottom portion of the basin-receiving recess of the coolant container. The plurality of positioning elements provided in the basin may include a plurality of recesses formed on an inner surface of a bottom portion of the basin, which in turn correspond to the plurality of protrusions on the outer surface of the bottom portion of the basin that is configured to contact the coolant container. The plurality of protrusions are preferably configured to be inserted within the plurality of recesses formed in the bottom portion of the basin-receiving recess of the coolant container. The plurality of positioning elements provided in the cradle may include a plurality of protrusions formed on a bottom portion of the cradle that are configured to be inserted within the plurality of recesses formed on the inner surface of the basin.

According to exemplary implementations, the plurality of positioning elements in the coolant container may line up linearly in a stacking direction with corresponding positioning elements formed in the basin and the cradle when provided in the single predetermined orientation relative to one another.

The basin-receiving recess of the coolant container, the basin and the cradle may each have an asymmetrical shape in plan view.

The plurality of recesses formed in a bottom portion of the basin-receiving recess of the coolant container may include a central recess and one or more smaller cross-section recesses provided around the central recess. The outer surface of the basin may be provided with a main protrusion that is shaped to fit within the central recess of the coolant container.

According to exemplary embodiments, the cradle may be positioned within the basin such that an organ holding surface of the cradle is substantially perpendicular to the stacking direction when in the single predetermined orientation. The organ or tissue holding surface of the cradle may or may not be watertight. The cradle may also include a peripheral ridge that surrounds a recessed organ or tissue holding surface. A width of the cradle may be wider than a depth of the recessed organ or tissue holding surface. The peripheral ridge may include a plurality of slits through which straps (netting) may be provided and may include a plurality of notches that are configured with protrusions for securing the straps to hold the organ or tissue in place. The peripheral ridge of the cradle may be spaced apart from side walls of the basin when positioned in the single predetermined orientation.

In some embodiments, the plurality of protrusions formed in the bottom portion of the cradle may be configured to be clearance fit within the plurality of recesses provided in the inner surface of the basin. Likewise, the plurality of protrusions formed in the outer surface of the bottom portion of the basin may be configured to be clearance fit within the plurality of recesses formed in the bottom portion of the basin-receiving recess of the coolant container. Alternatively, the plurality of protrusions formed in the bottom portion of the cradle or basin may be snap-fit or friction-fit (preferably releasable) within corresponding recesses in the basin or coolant container. The plurality of protrusions formed in the bottom portion of the cradle may contact and rest on the inner surface of the basin.

In some embodiments, the basin may be removably provided within the basin-receiving recess of the coolant container and the cradle may be removably provided within the basin. Alternatively, the cradle may be fixedly attached to the basin when inserted into the basin and subsequently moved with the basin.

In some embodiments, a perfusate recirculating flow path may be provided that connects to the basin.

According to exemplary implementations, an organ transporter may be provided that includes apparatus for holding an organ or tissue of the invention. The organ transporter is portable for carrying organs or tissues from place to place, and is sized to be carried by one or two persons and loaded into an automobile or small airplane. The organ transporter may have dimensions, for example, that are smaller than length 42 inches×width 18 inches×height 14 inches and may, for example, weigh less than 90 lbs, which includes the weight of the complete loaded system (for example, transporter, disposable components, organ, coolant and 3 liters of perfusate solution).

According to exemplary implementations, a disposable component kit may be provided. The kit may include a basin and at least one cradle that is shaped to fit within the basin and that is configured to hold an organ or tissue. Alternative cradles for different organs may be included in the kit. Each cradle is preferably generally a concave, symmetrical or asymmetrical bowl tailored to the anatomical particular organ. Cradles may be sized to accommodate a range from the smallest pediatric-neonatal up to the largest adult size organ. Preferably, the basin and the at least one cradle each have a plurality of positioning elements that are oriented such that the at least one cradle is keyed to fit within the basin in a single predetermined orientation relative to one another. Further, the plurality of positioning elements on the basin may include a plurality of protrusions on an outer surface of the basin.

According to exemplary implementations, the disposable components of the kit, as well as packaging that holds the disposable components, are preferably first cleaned and sterilized. The sterilized, disposable components may then be placed inside of the packaging and the kit may be sealed such that the packaging protects the sterilized, disposable components from being contaminated. Once the components are ready for use, the kit may be opened and the disposable components may be used with the organ perfusion apparatus. This allows the sterilized, disposable components to be "single-use" components. That is, once an organ is removed from the cradle and basin, the sterilized, disposable components may be discarded and replaced without being used for another organ. Accordingly, the organ perfusion apparatus maintains strict sterility and prevents contamination of an organ being perfused, diagnosed, treated, transported, and/or stored in the organ perfusion apparatus According to exemplary embodiments, the at least one cradle of the kit may include two or more cradles that are sized to hold different sized organs or tissue and that may be alternately placed in the basin in the single predetermined orientation based on the size of the organ or tissue.

In exemplary embodiments, the kit may include a plurality of straps (netting) in the packaging. The peripheral ridge of the at least one cradle preferably includes a plurality of slits through which the plurality of straps are provided and a plurality of notches that are configured with protrusions for securing the plurality of straps to hold the organ or tissue in place. The plurality of straps may also be secured in other ways, such as by using Velcro (hook and loop) or other types of securing means.

FIG. 1 is a schematic diagram of an exemplary perfusion apparatus 10 for an organ 20. The organ 20 may preferably be a liver, kidney, heart, lung or intestine, but may be any human or animal, natural or engineered, healthy, injured or diseased organ or tissue. The apparatus includes a basin 30 in which the organ may be placed. The basin 30 may hold a cradle 60 (see FIG. 9), which preferably includes a surface 60a on which the organ 20 is disposed when the organ 20 is in the apparatus 10. The basin 30 may include a first filter 33 that can function as a gross particulate filter. The basin 30 and/or the cradle 60 are preferably configured to allow a perfusate bath to form around the organ 20. The basin 30 or apparatus 10 may also include a temperature sensor 40 located or focused in or near the cradle 60. The basin 30 or apparatus 10 may include multiple temperature sensors 40, which may provide redundancy in the event of a failure and/or may provide temperature measurement at multiple locations. Preferably, the temperature sensor 40 is an infrared temperature sensor. The temperature sensor 40 is preferably disposed as close as practical to the organ 20 when the organ 20 is disposed in the cradle 60 in order to improve usefulness and accuracy of the temperature sensors 40, which preferably provide a temperature measurement of the perfusate that may be correlated to a temperature of the organ 20. Alternatively or additionally, the temperature sensor 40 may be used to directly measure the temperature of the organ 20.

Figure 8:
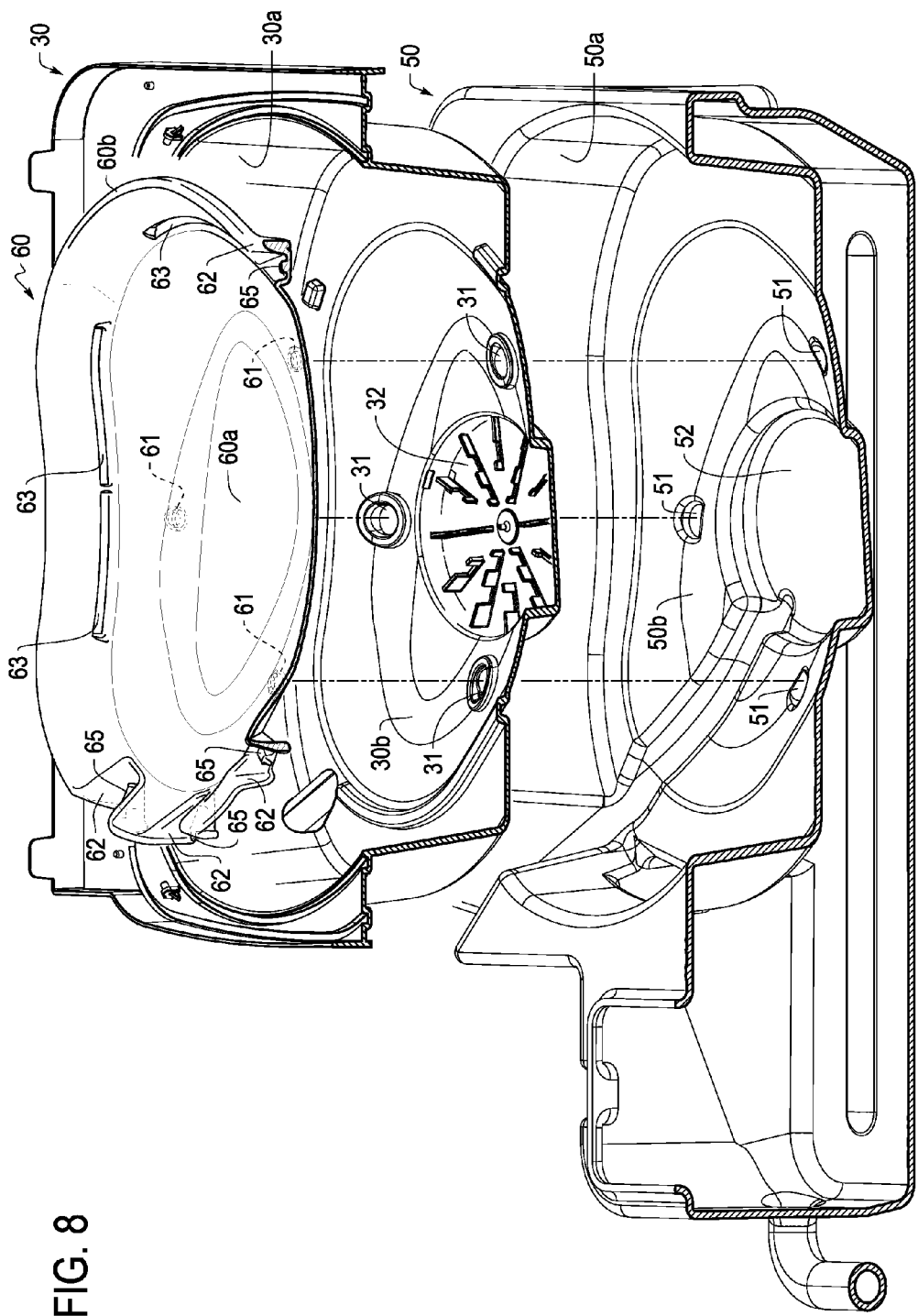
FIG. 8 is an exploded view illustrating how the cradle, basin and coolant container fit together in a predetermined orientation according to one embodiment.

The basin 30 is preferably disposed within an insulating coolant container 50 that may contain cold materials such as ice, ice water, brine or the like. Coolant container 50 may be permanently or removably attached to, or an integral, monolithic part of, apparatus 10. Thus, in use, the organ 20 is disposed within the cradle 60, which is disposed within the basin 30, which is disposed within the coolant container 50, as shown in FIG. 8. Preferably, each of the cradle 60, basin 30, and coolant container 50 is configured, or keyed, to fit within its corresponding mating component(s) in a single predetermined orientation relative to each other. The expression "single predetermined orientation" means that the cradle 60, the basin 30, and the coolant container 50 only fit within each other in one configuration relative to one another, and cannot rotate with respect to each other when stacked together. The configuration of the coolant container 50, basin 30 and cradle 60 preferably provides a configuration that provides cooling for the organ 20 without the contents of coolant container 50 contacting the organ 20 or the cradle 60. Although the coolant container 50 is described herein as containing ice or ice water, any suitable cooling medium can be used. Ice or ice water may be preferable due to the ease with which ice can be procured, but one of ordinary skill would understand that any suitable cooling medium, which could be an active cooling medium (such as a thermo electric cooler or a refrigerant loop) or a passive cooling medium similar to ice or ice water, or a combination thereof, may be utilized. The amount of ice, or other cooling medium, that can be placed within the coolant container 50 should be determined based upon the maximum time that cooling is to be provided while the organ 20 will be in the apparatus 10.

The cradle 60 may include components configured to securely restrain the organ 20 in place. Such components may, for example, include user selectable netting (straps 64) that is fastened to the cradle 60 (see FIG. 9). The user selectable netting or straps 64 keep the organ 20 in place while the organ 20 is manipulated or moved. For example, the organ may be held in place with the netting or straps 64 on the cradle 60 while being manipulated (e.g., vasculature trimmed, cannulas attached, or the like) before being placed in the basin or perfusion apparatus. Similarly, the organ may be held in place when the organ 20 is moved with the cradle 60 into the basin 30, when the basin 30 is moved into the coolant container 50 and when the apparatus 10 itself is moved during transport.

In the exemplary perfusion apparatus 10 of FIG. 1, after passing through the filter 33, the perfusate flows along a first flow path 70 that includes a suitable fluid conduit 72, such as flexible or rigid tubing, a pump 80, a pressure sensor 90, a second filter 34, an optional oxygenator 100 and a bubble trap 110, each of which is discussed below.

The first filter 33 is preferably a relatively coarse filter (relative to the second filter 34). Such a coarse filter may be provided to prevent large particles, which may for example be byproducts of the organ or of the organ being removed from the donor, from entering and clogging fluid paths of the apparatus 10. The first filter 33 may be an integral part of the basin 30 or the first filter 33 may be disposed elsewhere in the first flow path 70 downstream of the basin 30. For example, the first filter 33 may also be a separate component from the basin 30 or disposed within the fluid conduit 72.

The first flow path 70 may also include a pump 80. The pump 80 may be any pump that is suitable in connection with perfusing of organs. Examples of suitable pumps may include hand operated pumps, centrifugal pumps and roller pumps. If a roller pump is included, the roller pump may include a single channel or flow path (where only one tube is compressed by the rollers) or the roller pump may include multiple, parallel channels or flow paths (where multiple tubes are compressed by the rollers). If multiple, parallel channels or flow paths are included, the rollers may preferably be disposed out of phase or offset so that pulses created by the rollers are out of phase, which may result in a fluid flow out of the roller pump that is relatively less pulsatile than would be the case with a single roller. Such a multiple channel roller pump may achieve a constant flow rate or a minimally pulsatile flow rate, which may be advantageous depending on the other components in the flow path and/or the type of organ being perfused.

The flow path 70 may include a pressure sensor 90. The pressure sensor 90 may preferably be disposed after the outlet of the pump 80 in order to monitor and/or be used to control the pressure produced at the outlet of the pump by way of a suitable controller. The pressure sensor 90 may provide continuous or periodic monitoring of pressure.

The flow path 70 may include an oxygenator 100 such as an oxygenator membrane or body to provide oxygenation to the perfusate. Oxygen may be provided to the oxygenator 100 by any suitable means. Suitable oxygen sources may include pure oxygen or mixed gases such as air. The gas may be compressed, such as in a high-pressure cylinder, liquefied as would be stored in a dewar, or drawn from the surrounding atmosphere. Preferably, the oxygen may be provided by way of an oxygen generator, which may be separate from the apparatus 10 or integral to the apparatus 10. Oxygen may be generated through any suitable means, some examples of which include through pressure swing adsorption using a molecular sieve, through a ceramic oxygen generator (a solid state oxygen pump) or through decomposition of water.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow. The bubble trap 110 may include a volume of gas, initially or through the accumulation of bubbles, such that pressure fluctuations in the perfusate are dampened or eliminated.

The bubble trap 110 may include a vent that allows purging of gas during start up or a purging process. The vent may be connected to or part of purge flow path 140 (which is discussed in detail below). The vent is preferably open during a start up process so that any air or other gas may be purged from the perfusate path 70. Once the gas is purged from the perfusate path 70, the vent may preferably be closed. The vent may be closed manually or may be closed automatically by way of a suitable controller.

The bubble trap 110 may include a level sensor 112. A level sensor 112 may optionally be used during the purging process to determine when the purging is complete and/or may be used to determine when the purging process needs to be repeated, which may happen after bubbles have been trapped in the bubble trap 110. Also, through the use of the level sensor 112 and the vent, the accumulator function of the bubble trap can be tuned to account for differing amplitudes and frequencies of pulsatility in the perfusate flow.

The bubble trap 110 may have any number of outlets, as needed for a given application of the perfusion apparatus. In FIG. 1, three outlets are shown connected to three different flow paths, which may be particularly suited for the perfusion of a liver. When perfusing a liver, the three paths preferably include portal flow path 120 connected to the portal vein of a liver, hepatic flow path 130 connected to the hepatic artery of a liver, and bypass flow path 140 that provides a return path to the basin 30. There may also be a port in any fluid path that allows fluid access to the perfusate solution. The port may preferably be located in the bubble trap 110. This port may preferably include a luer type fitting such that a user may extract a small a sample of the perfusate for analysis. The port may also be utilized by a user to administer drugs to the perfusate without opening the basin.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs. Flow sensors 126, 136 may preferably be ultrasonic sensors disposed around tubing, although any suitable sensor may be used. Ultrasonic sensors may be advantageous because in normal usage such sensors do not come into contact with the perfusate and therefore are not in the sterile path. Such an implementation of ultrasonic sensors does not require replacement and/or cleaning after use.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Preferably, the bubble sensors 124, 134 are ultrasonic sensors disposed around tubing, although any suitable sensor may be used. Similar to pinch valves, ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles.

Flow control clamps 127, 137 may be used to fine-tune the flow rate in one or both of portal flow path 120 and hepatic flow path 130. Preferably, the organ provides self-regulation to control an amount of flow that exits the bubble trap 110 and is divided between the portal flow path 120 and the hepatic flow path 130. In such self regulated flow, pressure sensors 128, 138 provide overpressure monitoring. In the event that pressure delivered to the organ in either or both of the portal flow path 120 or the hepatic flow path 130 exceeds a predetermined threshold, the apparatus 10 can automatically stop and/or reduce the flow rate provided by the pump 80 to prevent damage to the organ. In addition or alternatively, the pressure sensors 128, 138 may be used to generate warning signals to the user and/or to an appropriate controller as pressures approach the predetermined threshold.

After exiting one or both of the portal flow path 120 and hepatic flow path 130, perfusate flows through the organ and returns to the basin 30 to form an organ bath.

Bypass flow path 140 may include a valve 142, and/or sensors such as oxygen sensor 144 and pH sensor 146. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 140 is only used during a purging or priming process, although it may also be used during perfusion, preferably continuously, to monitor perfusate properties in real time.

The organ perfusion apparatus 10 may also include an accelerometer 150. Preferably the accelerometer 150 is a three-axis accelerometer, although multiple single axis accelerometers may be used to the same effect. The accelerometer 150 may be used to continuously or periodically monitor and/or record the state of the apparatus 10. Monitoring may include monitoring for excessive shocks as well as attitude of the apparatus 10. By implementing such monitoring, misuse or potentially inappropriate conditions of the apparatus 10 can be detected and recorded.

The apparatus 10 may include storage compartments for items other than the organ 20. For example, the apparatus 10 may include a document compartment 160 to store documents and/or charts related to the organ 20. Also, the apparatus 10 may include one or more sample compartment. The sample compartment may be configured, for example, to store fluid and/or tissue samples. The sample compartment may be advantageously disposed near the coolant container 50 to provide cooling, which may be similar or equivalent to the cooling provided for the organ 20.

The apparatus 10 may include one or more tamper evident closures. A tamper evident closure may be used to alert a user that the apparatus 10 has been opened at an unauthorized time and/or location and/or by an unauthorized person. Evidence of tampering may alert the user to perform additional testing, screening, or the like before using the organ 20 and/or the apparatus 10.

Figure 2:
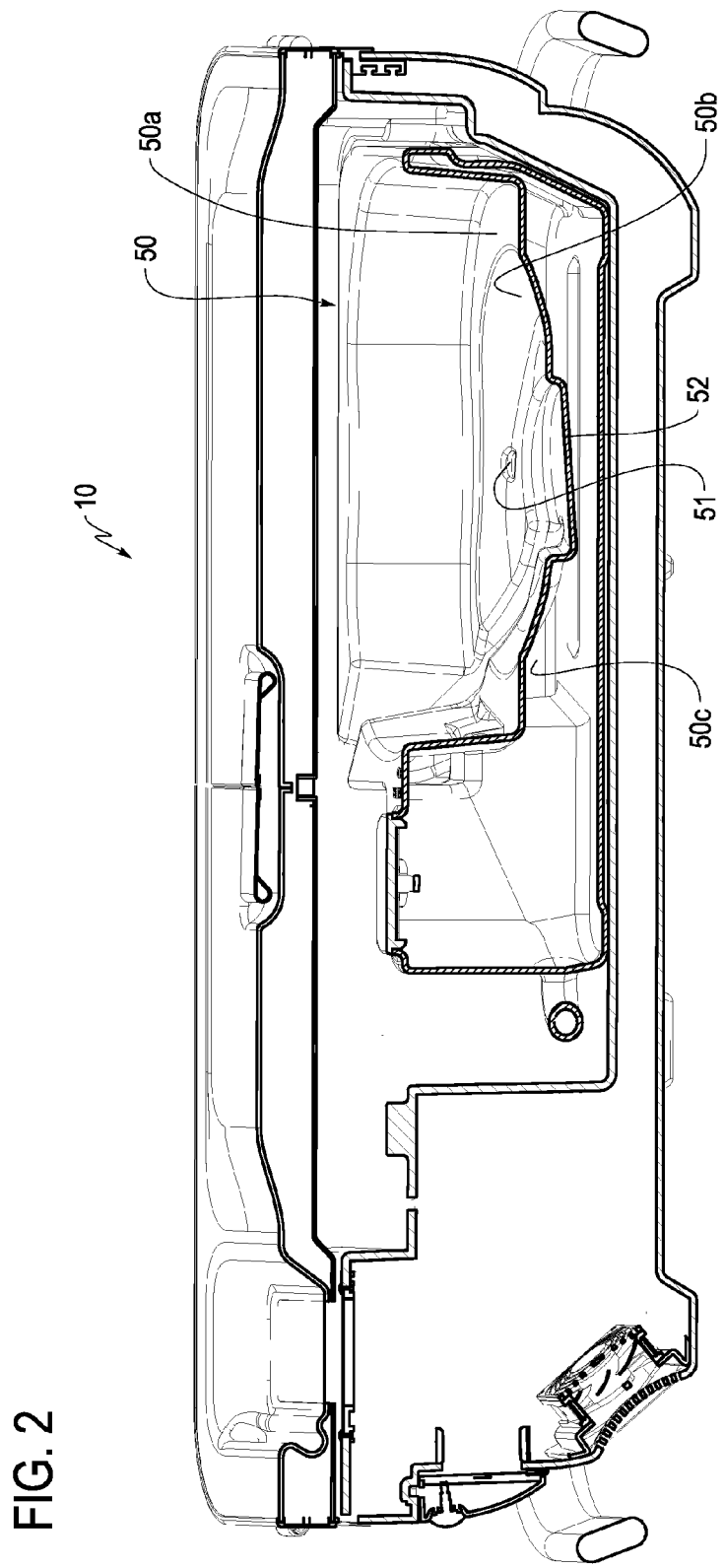
FIG. 2 is a cross sectional view of an organ perfusion apparatus according to one embodiment.
Figure 3:
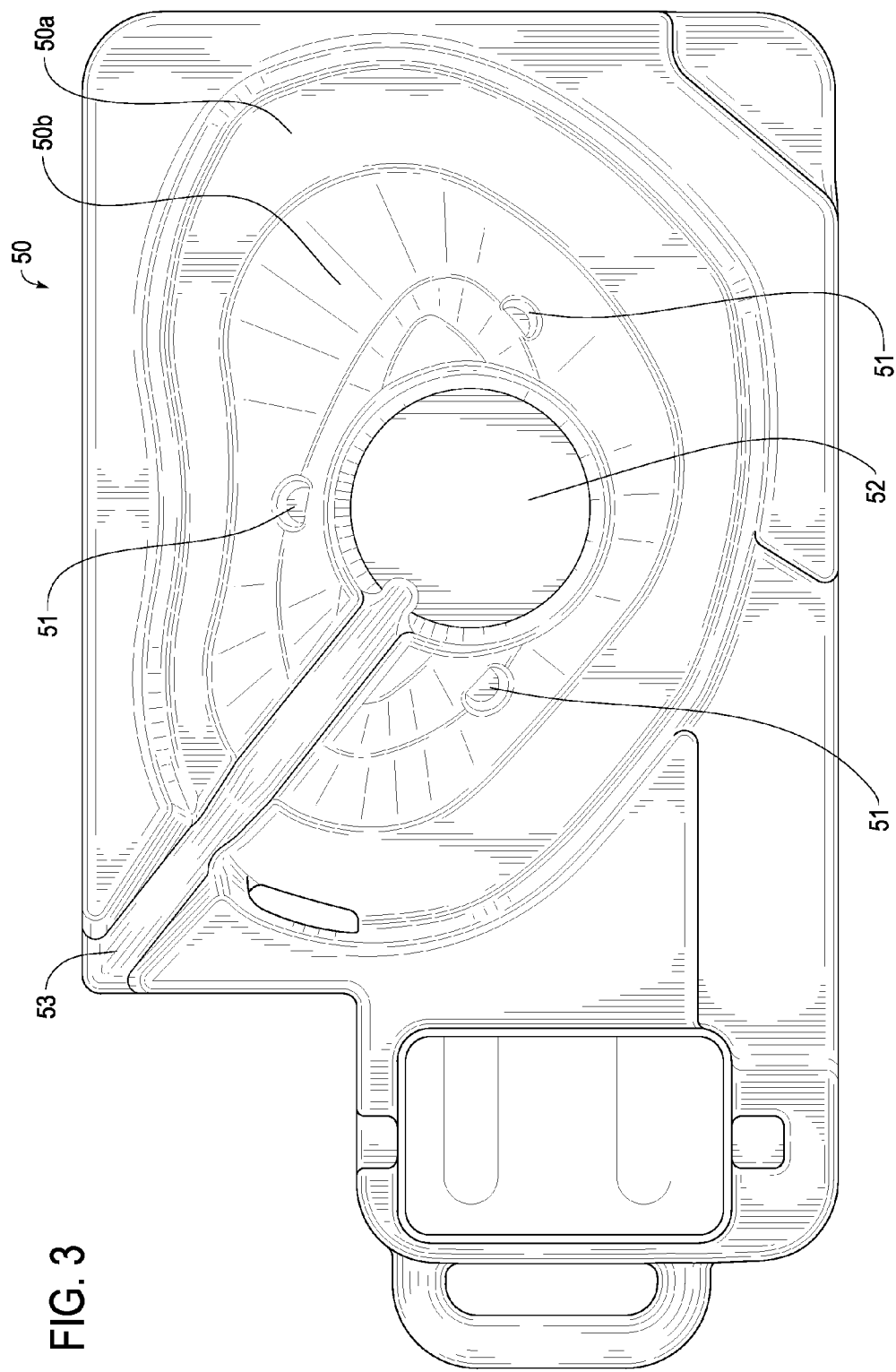
FIG. 3 is a top view of a coolant container according to one embodiment.

FIG. 2 is a cross-sectional view of the perfusion apparatus 10 according to one embodiment. The perfusion apparatus 10 preferably may be an organ transporter that is designed to be portable, for example, having dimensions smaller than length 42 inches×width 18 inches×height 14 inches and a weight less than 90 lbs, which includes the weight of the complete loaded system (for example, transporter, disposable components, organ, ice and 3 liters of perfusate solution). As seen in FIG. 2, the apparatus 10 includes the coolant container 50, which has an inner chamber 50c that is configured to contain the cooling medium. An outer surface of the coolant container 50 forms a basin-receiving recess 50a that is at least partly surrounded by the inner chamber 50c. A bottom portion 50b of the basin-receiving recess 50a of the coolant container 50 may include a plurality of recesses 51 and 52. For example, the plurality of recesses may include a central main recess 52 and multiple recesses 51 positioned around the main recess 52. FIG. 3 illustrates a top view of the coolant container 50. The embodiment illustrated in FIG. 3 has three recesses 51. However, more or fewer than three recesses 51 may be provided. Preferably the coolant container 50 is formed of any rigid plastic material with good thermal conduction properties, preferably an olefin material, and is preferably formed using a rotational molding process. As seen on FIG. 3, a channel 53 (for example, a channel configured to receive a perfusion conduit) may be provided in the coolant container 50. The channel 53 may be configured to accommodate tubing (not shown) that can be attached to the basin 30 and allows for circulation and filtration of perfusate fluid. While the positioning elements on the coolant container 50 are illustrated as recesses 51, it is understood that the positioning elements on the coolant container 50 may alternatively be protrusions that may mate with corresponding recesses on a bottom portion of the basin 30.

Figure 4:
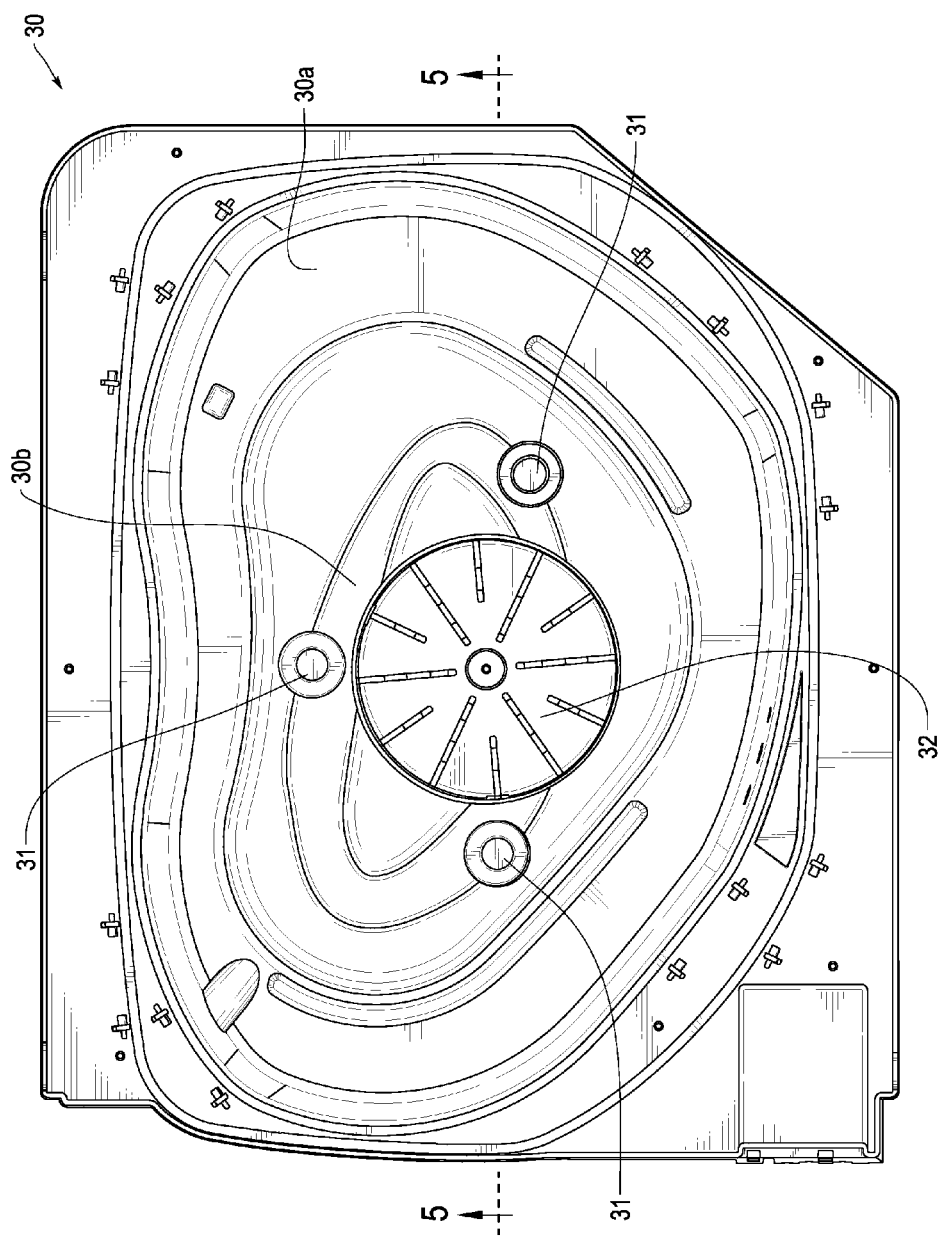
FIG. 4 is a top view of a basin according to one embodiment.
Figure 5:
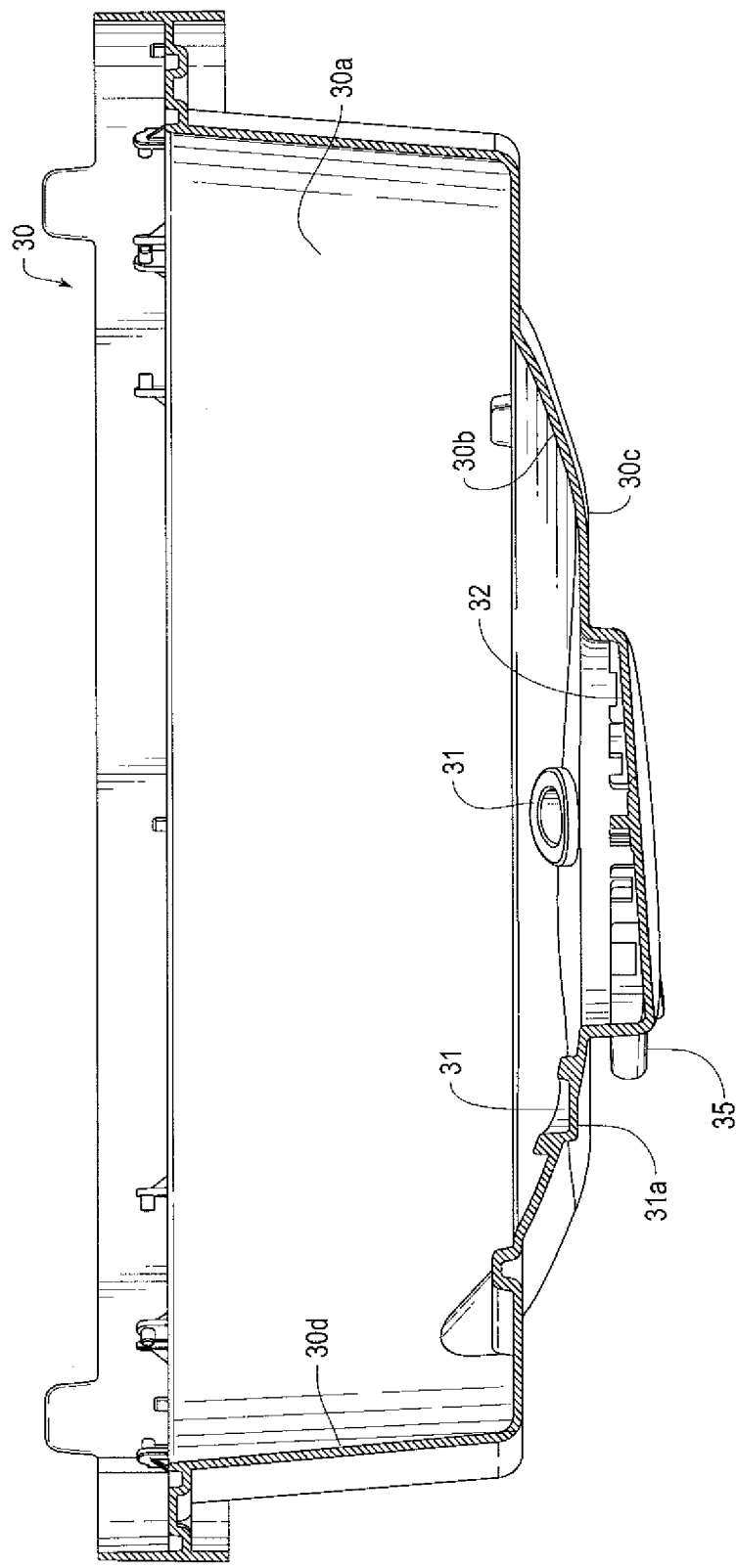
FIG. 5 is a cross-sectional view of the basin taken along lines 5-5 in FIG. 4.

FIG. 4 illustrates a top view of the basin 30 according to one embodiment. The basin 30 includes a watertight inner portion 30a including a bottom portion 30b. The bottom portion 30b of the basin 30 includes a plurality of recesses 31 and 32, which, similar to the coolant container 50, may include a main recess 32 and multiple recesses 31 surrounding the main recess 32. The basin 30 is preferably shaped to fit within the basin-receiving recess 50a of the coolant container 50 in a single predetermined orientation relative to the coolant container 50. FIG. 5 is a cross-sectional view of the basin 30 illustrated in FIG. 4. As seen in FIG. 5, the recesses 31 and 32 of the basin 30 define protrusions 31a on an exterior surface 30c of the basin 30 that are configured to line up with, and be inserted into, the plurality of recesses 51 and 52 formed in the basin-receiving recess 50a of the coolant container 50 when in the single predetermined orientation. The protrusions on the exterior surface 30c of the basin 30 may also be provided on a side surface of the basin 30 as an alternative or in addition to those provided on the bottom of the basin 30. In some embodiments, at least some of the plurality of protrusions 31a may also act as feet when the basin 30 is not provided within the coolant container 50 and is placed on a flat surface. In some embodiments, the protrusions 31a are sufficiently long to stably support the basin 30 when on a flat surface in spite of the exterior surface 30c otherwise being substantially not level. Preferably the basin 30 is formed of any rigid plastic material, preferably a thermoplastic, clear medical grade, nontoxic and biocompatible material such as polycarbonate, and is preferably formed using a plastic injection molding process. While the positioning elements on the basin 30 are illustrated as recesses 31, it is understood that the positioning elements on the basin 30 may alternatively be protrusions that may mate with corresponding recesses on a bottom portion of the cradle 60. Additionally, as shown in FIG. 5, a perfusate recirculation flow conduit 35 may connect to the basin.

Figure 6:
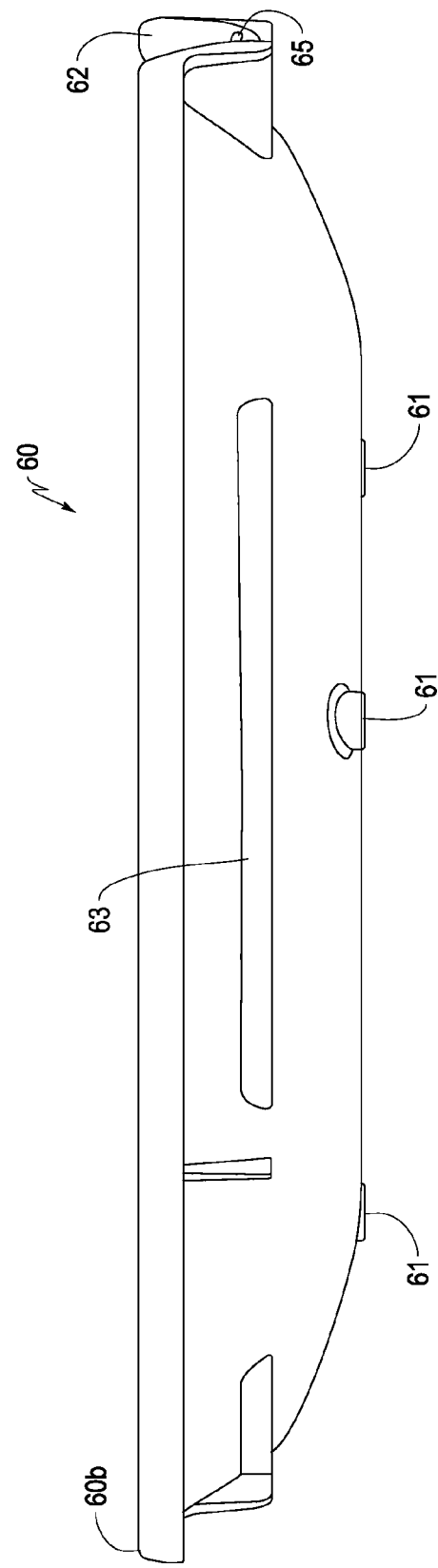
FIG. 6 is a side view of a cradle according to one embodiment.

FIG. 6 illustrates a side view of a cradle 60 that is shaped to fit within the basin 30 and is configured to hold the organ or the tissue. The cradle 60 may include a plurality of protrusions 61 formed on bottom exterior surface 60c thereof. Each of the plurality of protrusions 61 is preferably positioned so as to be keyed to fit within a corresponding recess 31 provided in the basin 30 in a single predetermined orientation relative to the basin 30. In some embodiments, the plurality of protrusions 61 may also act as feet when the cradle 60 is not provided within the basin 30 and is placed on a flat surface. In some embodiments, the protrusions 61 are sufficiently long to stably support the cradle 60 when on a flat surface in spite of the exterior surface 60c otherwise being substantially rounded. Preferably the protrusions 61 of the cradle 60 are clearance fit within the recesses 31 of the basin 30 such that the cradle may be easily removed from the basin, for example, during harvesting and/or preparation of the organ or tissue for transport. Alternatively, the protrusions 61 may be snap fit or compression fit within the recesses 31. It is preferred, but not required, that the cradle 60 can be readily removed from the basin 30. Preferably the cradle 60 is formed of any rigid plastic material, preferably a thermoplastic, clear medical grade, nontoxic and biocompatible material such as polycarbonate, and is preferably formed using a plastic injection molding process. Any process that can create a cradle 60 with surfaces that are controlled as they come into contact with the organ 20 and cannot damage that organ 20. Mechanical strength of the material is important to stabilize and support the organ 20 and netting anchor points.

Figure 7:
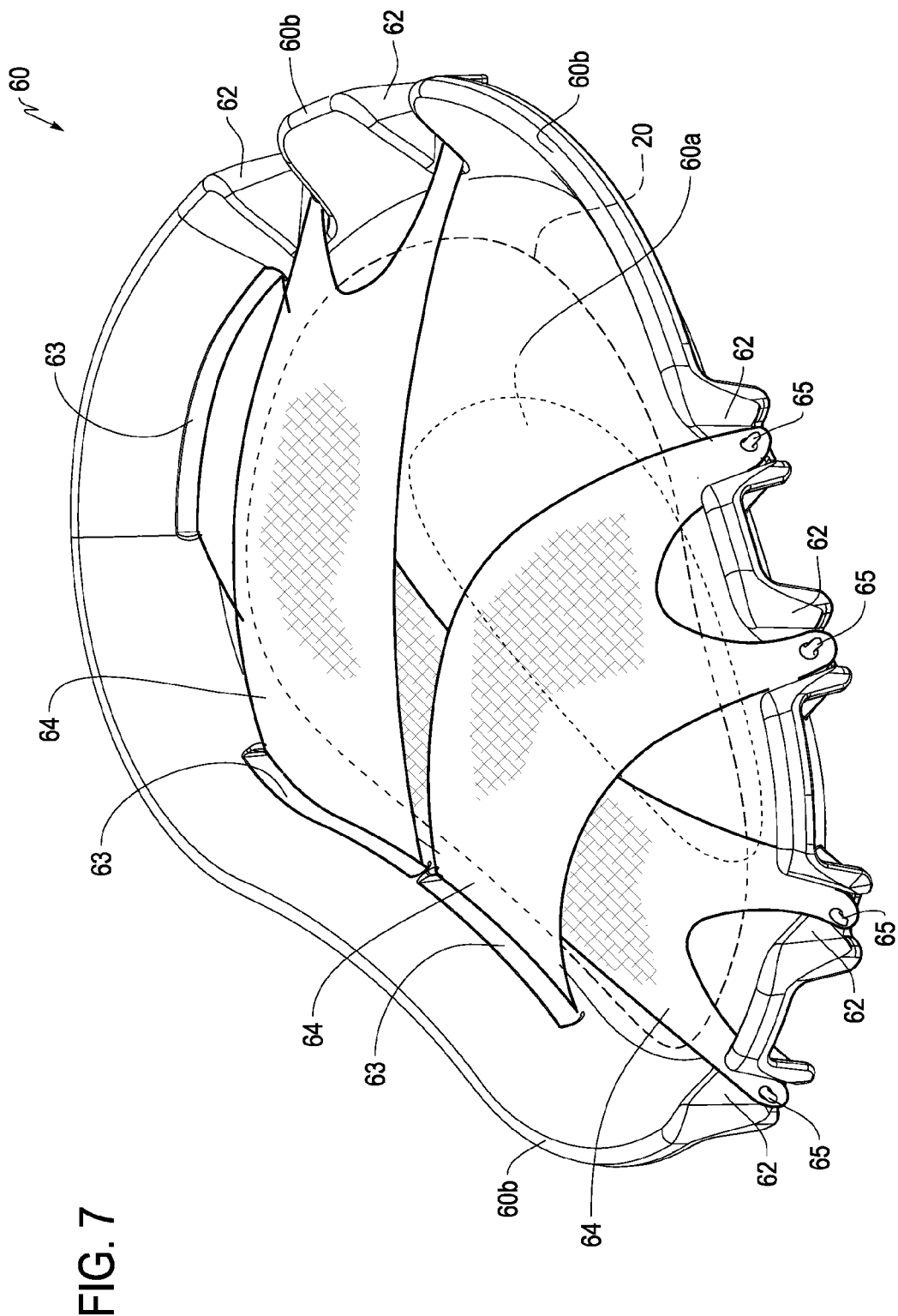
FIG. 7 is a perspective view of a cradle according to one embodiment.

As illustrated in FIG. 7, the cradle 60 includes a peripheral ridge 60b that surrounds a recessed organ or tissue holding surface 60a. The recessed organ or tissue holding surface 60a may be watertight. As seen in FIGS. 6 and 7, a width of the cradle may be wider than a depth of the recessed organ or tissue holding surface 60a. The organ or tissue holding surface 60a, as well as the cradle 60 itself, may be configured to be positioned substantially horizontally when provided in the single predetermined orientation in use. The peripheral ridge 60b may include a plurality of slits 63 through which a plurality of straps 64 may be provided and a plurality of notches 62 that are configured with protrusions 65 for securing the plurality of straps 64 (see FIG. 7) to hold the organ or tissue in place. As seen in FIG. 7, at least three slits 64 may be provided to hold the organ or tissue in place. As an alternative to the protrusions 65, the cradle 60 may only be provided with slits 63 and the plurality of straps 64 may be secured in another manner, such as by Velcro® (hook and loop fasteners) or any other suitable way of securing the straps 64. The plurality of straps 64 may be formed of netting that can be selected based on the size and/or shape of the organ or tissue. The peripheral ridge 60b of the cradle 60 may be spaced apart from side walls 30d of the basin 30 when the cradle 60 is in the predetermined orientation (see FIG. 9).

FIG. 8 illustrates an exploded view of how the cradle 60, basin 30 and coolant container 50 fit together in the predetermined orientation. The dashed lines indicate how the respective protrusions/recesses in each of the cradle 60, basin 30 and coolant container 50 line up. As seen in the embodiments of FIG. 8, respective protrusions/recesses line up in a stacking direction. The shape of each of the cradle 60, basin 30 and basin-receiving recess 50a may be an asymmetrical shape to facilitate visual orientation of each with respect to the adjacent ones. For example, the shape may be similar to a shape of an organ to be held on the organ holding surface 60a. Generally nesting concave cradle 60, basin 30 and recess 50a, which are in close proximity to one another, aids the conduction of heat (thermal transfer) through the fluid medium. The basin 30 may be in direct contact with the coolant container 50. The preferred shape generally conforms to the average shape of an organ such as a human liver. The shape could be any other shape, including round, square, oval and symmetrical so long as the shape keeps the organ in a secure orientation. While the positioning elements on the cradle 60 are illustrated as protrusions 61, it is understood that the positioning elements on the cradle 60 may alternatively be recesses into which corresponding protrusions on the basin 30 may be inserted.

Figure 9:
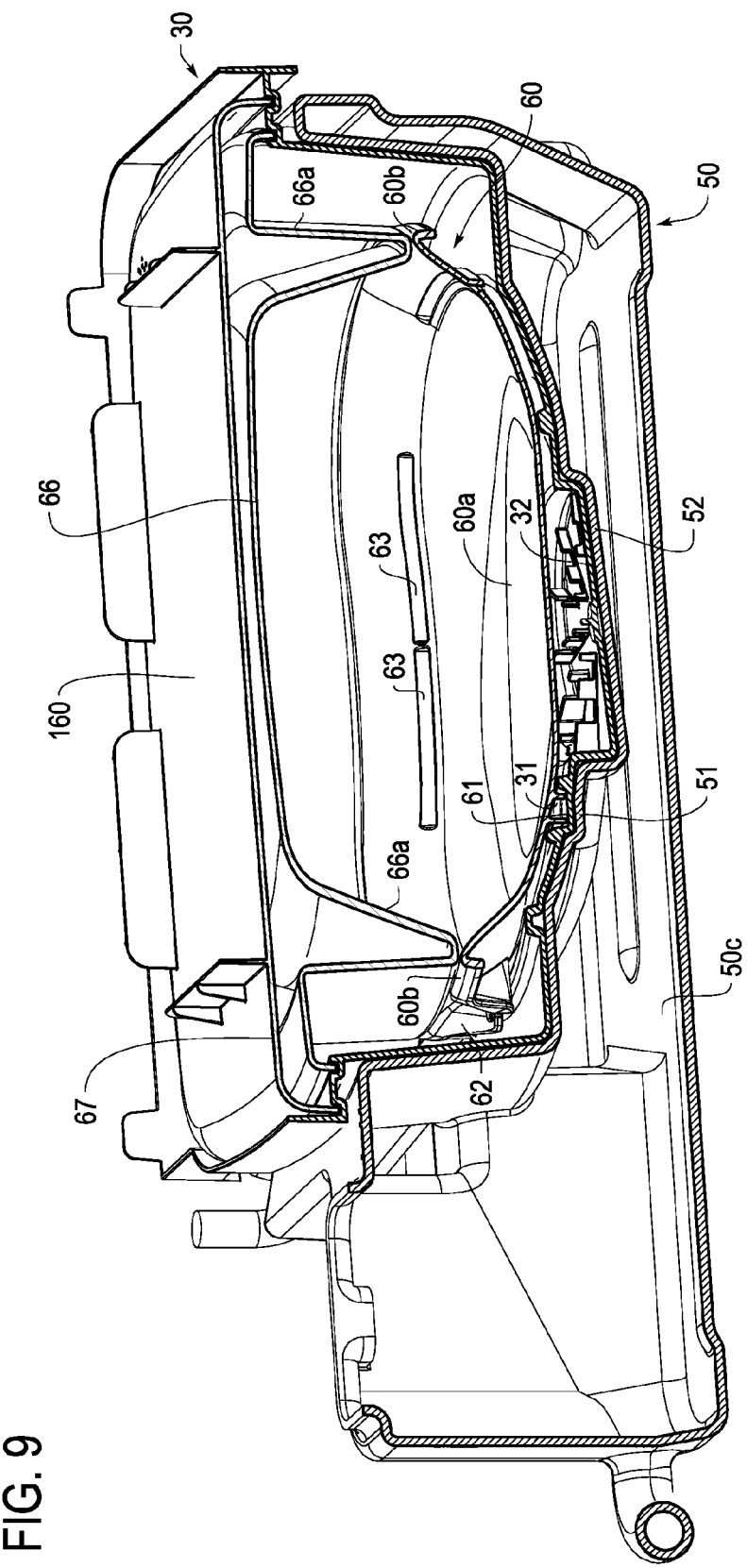
FIG. 9 is a cross-sectional view of the combined coolant container, basin and cradle of FIG. 8 while in the predetermined orientation.

FIG. 9 illustrates a cross-sectional view of the cradle 60, basin 30 and coolant container 50 while in the predetermined orientation ready for use. The basin 30 is provided with a lid, preferably two lids, an inner lid 66 and an outer lid 67. As seen in FIG. 9, the inner lid 66 and the outer lid 67 may be provided on an upper surface of the basin 30. The inner lid is sized to come in close proximity to the perimeter top surface of the cradle to help maintain stability of the organ in the event of mechanical impact and shock during transport. The lids 66 and 67 can create a substantially fluid-tight seal with the basin 30, and can prevent contamination. The lids 66 and 67 may also provide for a redundant airtight seal should the seal from either lid 66 or 67 fail. Both the inner lid 66 and outer lid 67 preferably contain an air vent (for example, a porous hydrophobic membrane) that allows for gas transfer in order to maintain pressure equilibrium. The inner lid 66 may have a downwardly protruding extension 66a that matches a circumferential shape of the peripheral ridge 60b and is configured to contact the peripheral ridge 60b and help hold the cradle 60 in position.

Figure 10:
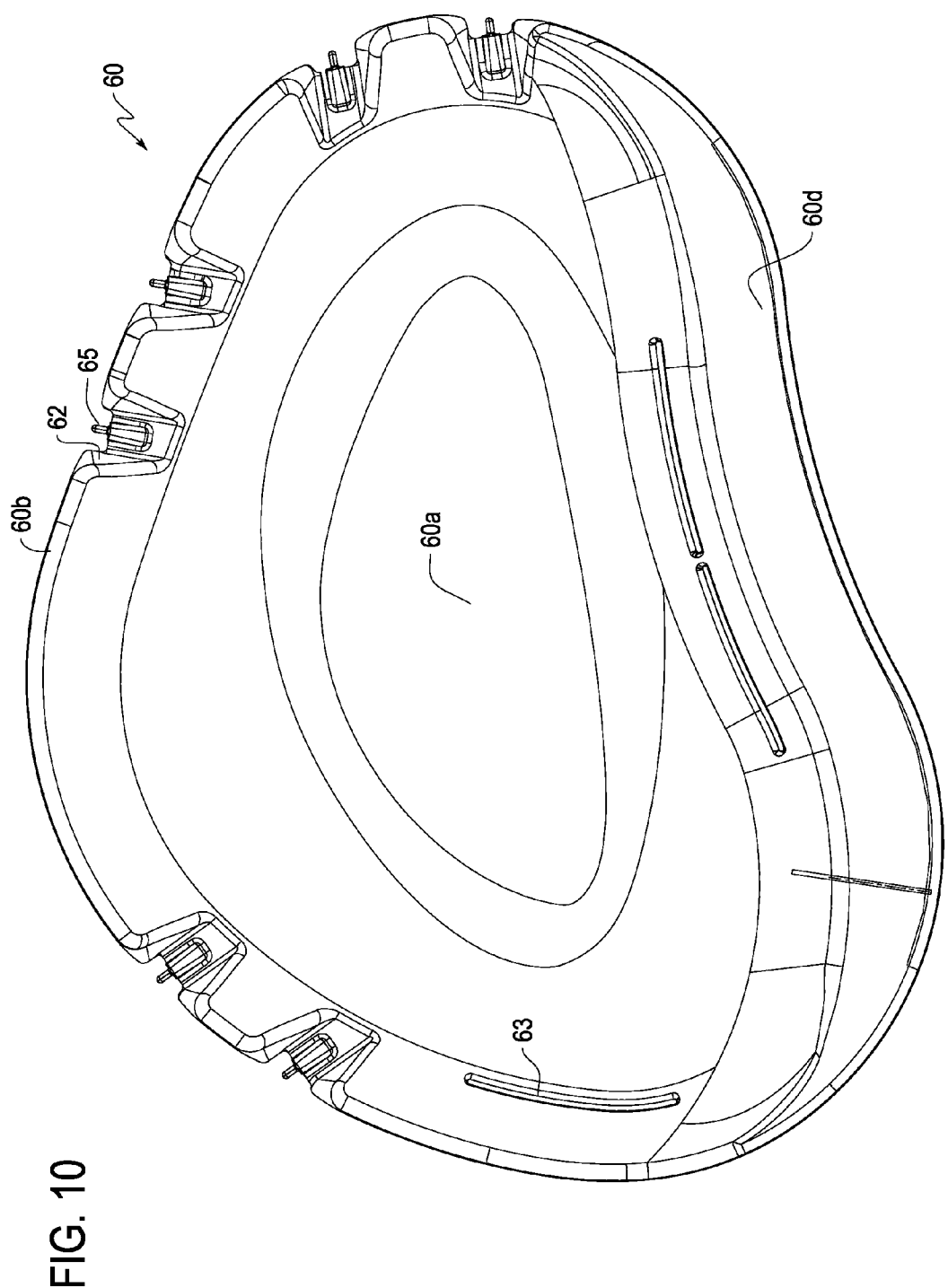
FIG. 10 is a top view of a cradle configured for a first sized and/or shaped organ according to one embodiment.
Figure 11:
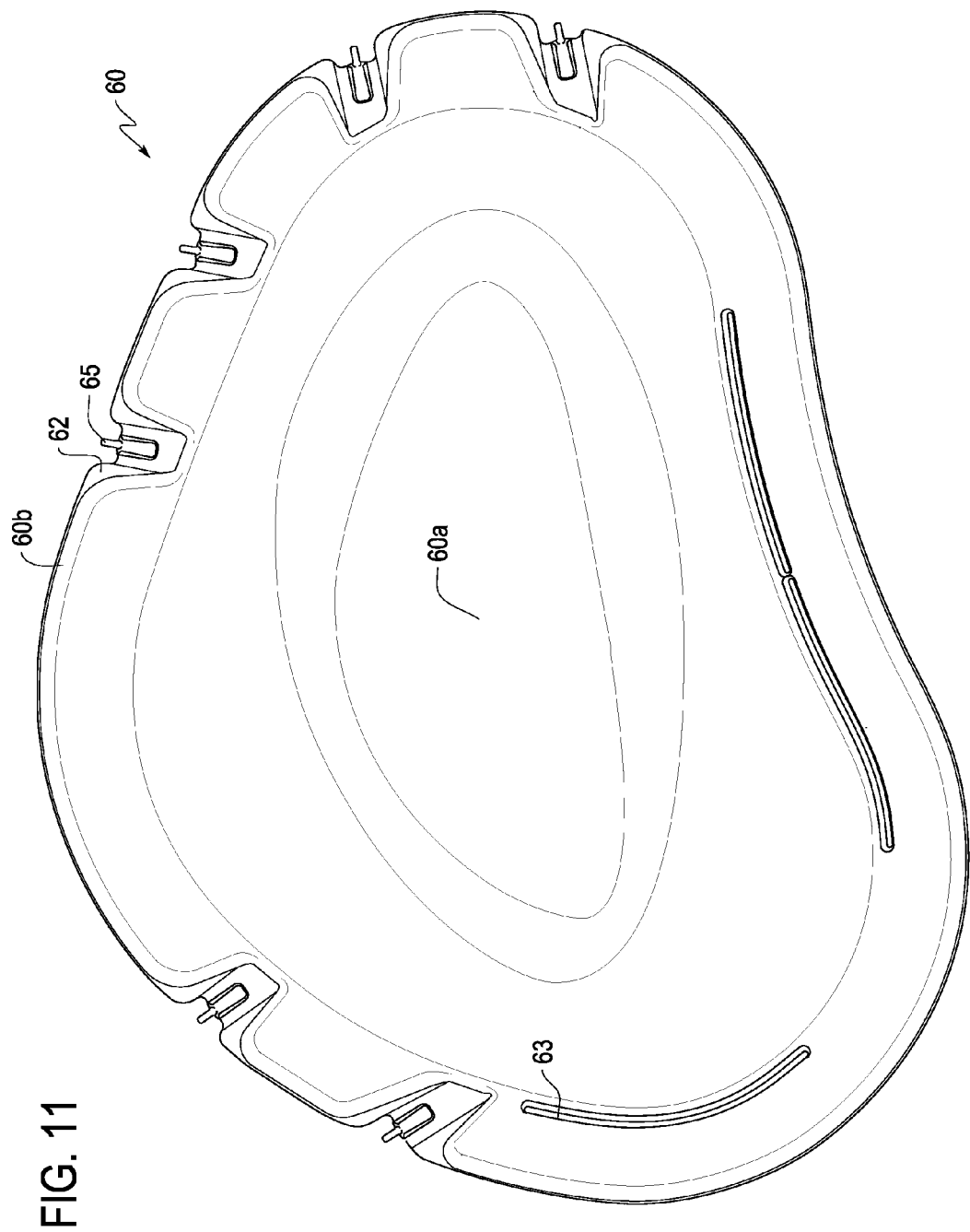
FIG. 11 is a top view of a cradle configured for a second sized and/or shaped organ according to one embodiment.

FIGS. 10 and 11 illustrate two different embodiments of cradles 60 that are sized and/or shaped to hold organs and/or tissues of different sizes. As seen in FIG. 10, the surface 60a on which the organ 20 is preferably disposed is smaller than the surface 60a in FIG. 11 due to a thicker peripheral ridge portion 60d on one side.

Preferably, all components of the apparatus 10 that come into contact with perfusate and/or the organ 20 are disposable and/or easily replaced. Such disposable items may be included in one or more kit or saleable package. For example, such a kit may include packaging such as plastic or shrink wrap packaging containing some or all of the components that come into contact with an organ 20 and/or perfusate. In embodiments, the tubing, filter, oxygenator and bubble trap are packaged together, and the cradle and basin are packaged individually or together, and optionally together with the tubing, filter, oxygenator and bubble trap in a manner preconfigured to be placed into a flow path arrangement of fixed-location parts in apparatus 10. The kit may include multiple differently sized and/or shaped cradles 60 to accommodate different sized organs. Including such different cradles 60 may be beneficial, for example, with livers or other organs that may have varying sizes and shapes. FIGS. 10 and 11 illustrate two different versions of the cradle 60.

The sterilized disposable kit may comprise the basin 30 and one or more cradle 60 inside packaging such as a bag, box or shrink wrap material. The kit may also include the plurality of straps 64, the first filter 33, and the second filter 34. The sterilized disposable kit may further include other disposable components such as the inner lid 66 and tubing or other parts that come into contact with the perfusate or the organ. The disposable components, as well as the container that holds the disposable components, are preferably first cleaned and sterilized. The sterilized, disposable components may then be placed inside of the container and the kit may be sealed such that the container protects the sterilized, disposable components from being contaminated. Once the components are ready for use, the kit may be opened and the disposable components may be used with the organ perfusion apparatus 10. This allows the sterilized, disposable components to be "single-use" components. That is, once an organ 20 is removed from the cradle 60 and basin 30, the sterilized, disposable components may be discarded and replaced without being used for another organ. Accordingly, the organ perfusion apparatus 10 maintains strict sterility and prevents contamination of an organ 20 being perfused, transported, diagnosed, treated and/or stored in the organ perfusion apparatus 10.

What has been described and illustrated herein are preferred embodiments of the invention along with some variations. The terms, descriptions and figures used herein are set forth by way of illustration only and are not meant as limitations. Those skilled in the art will recognize that many variations are possible within the spirit and scope of the invention.

What is claimed is:

1. An apparatus for holding an organ or tissue for at least one of perfusion, storage, diagnosis, treatment and transport of the organ or tissue, the apparatus comprising:
   a coolant container having a first surface and a second surface, the first surface defining an inner chamber that is configured to contain a coolant, the second surface forming a basin-receiving recess that is at least partly surrounded by the inner chamber;
   a basin that is shaped to fit within the basin-receiving recess of the coolant container; and
   a cradle that is shaped to fit within the basin and is configured to hold the organ or tissue, wherein
   the basin-receiving recess of the coolant container, the basin and the cradle each have a plurality of positioning elements that are oriented such that the cradle is keyed to fit within the basin and the basin is keyed to fit within the coolant container in a single predetermined orientation with respect to each other,
   the plurality of positioning elements of the basin includes a plurality of protrusions on a lower outer surface of the basin that are configured to be inserted into recesses on an inner surface of the coolant container,
   the plurality of positioning elements of the cradle includes a plurality of protrusions on a lower outer surface of the cradle that are configured to be inserted into recesses on an inner surface of the basin, and
   the plurality of protrusions on the lower outer surface of the cradle and the recesses on the inner surface of the basin are positioned asymmetrically so that the plurality of protrusions of the cradle can be aligned with the recesses of the basin in only the single predetermined orientation at which the cradle is keyed to fit within the basin.

2. The apparatus according to claim 1, wherein the recesses on the inner surface of the coolant container are included in the plurality of positioning elements of the basin-receiving recess of the coolant container.

3. The apparatus according to claim 2, wherein the plurality of positioning elements of the basin further includes the recesses on the inner surface of the basin, which in turn correspond to the plurality of protrusions on the lower outer surface of the basin.

4. The apparatus according to claim 3, wherein the plurality of positioning elements of the coolant container line up linearly in a stacking direction with corresponding said positioning elements of the basin and the cradle when in the single predetermined orientation.

5. The apparatus according to claim 1, wherein the basin-receiving recess of the coolant container, the basin and the cradle each have an asymmetrical shape in plan view.

6. The apparatus according to claim 2, wherein the plurality of recesses on the inner surface of the basin-receiving recess of the coolant container include a central recess and one or more smaller cross-section recesses provided around the central recess, and the lower outer surface of the basin has a main protrusion that is shaped to fit within the central recess of the coolant container.

7. The apparatus according to claim 1, wherein the cradle is configured to be positioned within the basin such that an organ or tissue holding surface of the cradle is substantially perpendicular to a stacking direction of the coolant container, basin and cradle when in the single predetermined orientation.

8. The apparatus according to claim 7, wherein the organ or tissue holding surface of the cradle is watertight.

9. The apparatus according to claim 1, wherein the cradle includes a peripheral ridge that surrounds a recessed organ or tissue holding surface.

10. The apparatus according to claim 9, wherein a width of the cradle is wider than a depth of the recessed organ or tissue holding surface.

11. The apparatus according to claim 9, wherein the peripheral ridge includes a plurality of slits that are configured to receive netting or straps to hold an organ or tissue in place in the cradle.

12. The apparatus according to claim 9, wherein the peripheral ridge of the cradle is spaced apart from side walls of the basin when the coolant container, cradle and basin are positioned in the single predetermined orientation.

13. The apparatus according to claim 3, wherein the plurality of protrusions of the cradle are configured to be clearance fit within the recesses on the inner surface of the basin.

14. The apparatus according to claim 2, wherein the plurality of protrusions of the basin are configured to be clearance fit within the recesses on the inner surface of the basin-receiving recess of the coolant container.

15. The apparatus according to claim 1, wherein the basin is removably provided within the basin-receiving recess of the coolant container and the cradle is removably provided within the basin.

16. The apparatus according to claim 1, wherein an organ supporting surface of the cradle has an asymmetrical shape in plan view.

17. The apparatus according to claim 1, wherein the protrusions on the lower outer surface of the cradle extend below an otherwise lowermost portion of the cradle and form feet on which the cradle may be stably supported on a flat surface when the cradle is not in the basin.

18. The apparatus according to claim 1, wherein the basin-receiving recess of the coolant container includes a channel that is configured to receive a perfusion conduit that extends between the basin and the coolant container when the coolant container, basin and cradle are in the single predetermined orientation.

19. The apparatus according to claim 1, further comprising:
a perfusate recirculation flow conduit that connects to the basin.

20. The apparatus for holding an organ or tissue according to claim 1, wherein the apparatus is transportable and weighs less than 90 pounds.

21. The apparatus for holding an organ or tissue according to claim 1, wherein the basin is in direct contact with sidewalls of the coolant container to aid in thermal conduction from the coolant container into the basin.

22. The apparatus for holding an organ or tissue according to claim 1, wherein
the cradle is a first cradle,
the apparatus for holding an organ or tissue further comprises a second cradle having a different size and/or shape than the first cradle, and
the second cradle includes a plurality of protrusions identical in shape and relative position to the plurality of protrusions of the first cradle so that the plurality of protrusions of the second cradle can also be aligned with the recesses of the basin.

* * * * *